US012746086B2

(12) United States Patent
Mitsui

(10) Patent No.: US 12,746,086 B2
(45) Date of Patent: Sep. 29, 2026

(54) ENDOSCOPE HOLDER

(71) Applicant: OLYMPUS MEDICAL SYSTEMS CORP., Tokyo (JP)

(72) Inventor: Hiroshi Mitsui, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 132 days.

(21) Appl. No.: 18/770,923

(22) Filed: Jul. 12, 2024

(65) Prior Publication Data

US 2025/0025256 A1 Jan. 23, 2025

Related U.S. Application Data

(60) Provisional application No. 63/527,838, filed on Jul. 20, 2023.

(51) Int. Cl.
*A61B 50/20* (2016.01)
*F16M 13/02* (2006.01)

(52) U.S. Cl.
CPC ............. *A61B 50/20* (2016.02); *F16M 13/02* (2013.01)

(58) Field of Classification Search
CPC ................................ A61B 50/20; F16M 13/02
See application file for complete search history.

(56) References Cited

U.S. PATENT DOCUMENTS

| | | | |
|---|---|---|---|
| 4,808,167 A | 2/1989 | Mann et al. | |
| 7,875,000 B2 | 1/2011 | Krebs et al. | |
| 9,138,524 B2 | 9/2015 | Bluchel et al. | |
| 11,382,495 B2 * | 7/2022 | Awadu | A61B 1/0014 |
| 2023/0000323 A1 * | 1/2023 | Yahagi | A61B 1/00071 |
| 2023/0277350 A1 * | 9/2023 | Baker | A61F 5/0079 604/9 |
| 2023/0285614 A1 * | 9/2023 | Kotani | A61B 50/13 |
| 2023/0310098 A1 * | 10/2023 | Sonoda | A61B 1/00158 |

FOREIGN PATENT DOCUMENTS

| | | |
|---|---|---|
| JP | H05-095888 A | 4/1993 |
| JP | 3461225 B2 | 10/2003 |
| JP | 6714960 B2 | 7/2020 |

* cited by examiner

*Primary Examiner* — Md N Haque

(74) *Attorney, Agent, or Firm* — Morgan, Lewis & Bockius LLP

(57) ABSTRACT

An endoscope holder includes a holder body, a hanger and a slide member. The hanger is pivotably attached to the holder body to move between a first angle position and a second angle position. The slide member is supported on the holder body. The slide member is configured to move slidably between a first position and a second position. At the first position, the slide member restricts pivoting of the hanger from the first angle position to the second angle position. At the second position, the slide member permits pivoting of the hanger from the first angle position to the second angle position. When the hanger is at the first angle position, the hanger is configured to support an endoscope by hanging the endoscope on the hanger. When the hanger is at the second angle position, the hanger is configured to not support the endoscope by hanging.

20 Claims, 11 Drawing Sheets

ENDOSCOPE HOLDER

CROSS-REFERENCE TO RELATED APPLICATION DATA

This application is based on and claims priority under 35 U.S.C. § 119 to U.S. Provisional Application No. 63/527,838, filed on Jul. 20, 2023, the entire contents of which are incorporated herein by reference.

BACKGROUND

The present disclosure relates to an endoscope holder used to hang and hold an endoscope.

DESCRIPTION OF THE RELATED ART

An endoscope may undergo pre-use checks by being connected to an endoscope system. The pre-use checks are carried out, for example, with the endoscope being hung on and held to an endoscope holder of an endoscope system cart.

Japanese Patent No. 3461225 describes an endoscope cart provided with a holding portion for use to hold at least part of an endoscopic scope and used to transport an endoscope apparatus.

Such conventional endoscope holders are generally fixed to an endoscope system cart. A used endoscope can also be hung on an endoscope holder. Thus, to prevent cross infection via the endoscope holder, the endoscope holder is reprocessed before a new endoscopic examination.

Incidentally, in recent years, a single-use endoscope discarded after a single use has been proposed. The single-use endoscope is shipped under sterile conditions by being sealed in a sterile pack and is taken out of the sterile pack before an endoscopic examination. On the other hand, a reusable endoscope holder is reprocessed before an endoscope is hung on the holder.

SUMMARY

An endoscope holder according to one aspect of the present disclosure includes: a holder body; a hanger pivotably attached to the holder body to move between a first angle position and a second angle position; and a slide member supported on the holder body, the slide member configured to move slidably between a first position and a second position. Wherein, at the first position, the slide member restricts pivoting of the hanger from the first angle position to the second angle position and, at the second position, the slide member permits pivoting of the hanger from the first angle position to the second angle position. Wherein, when the hanger is at the first angle position, the hanger is configured to support an endoscope by hanging the endoscope on the hanger and, when the hanger is at the second angle position, the hanger is configured to not support the endoscope by hanging.

DETAILED DESCRIPTION

Figure 1:
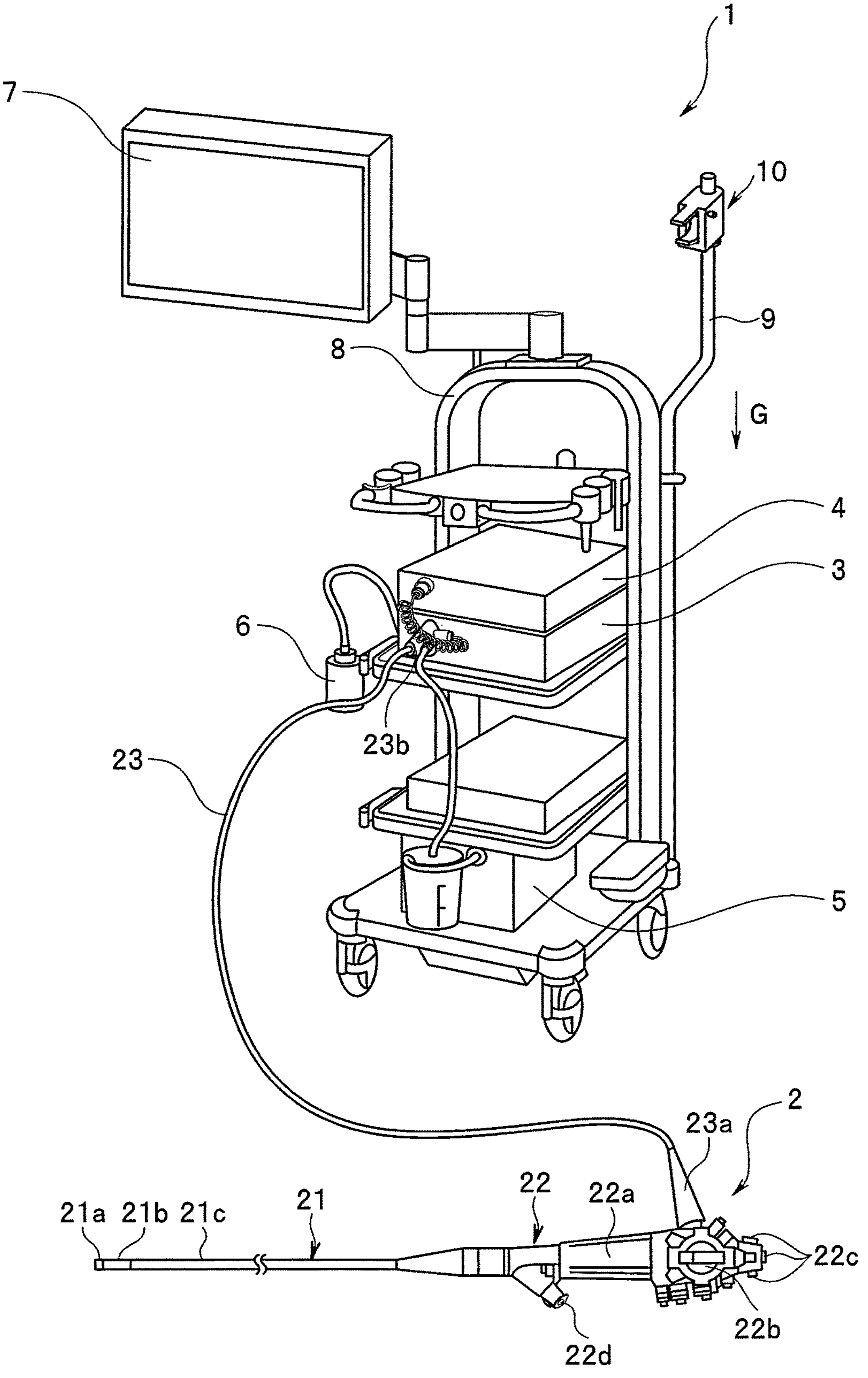
FIG. 1 is a perspective view showing a configuration of an endoscope system according to a first embodiment of the present disclosure.

Generally, the need for pre-use reprocessing of an endoscope holder used in carrying out pre-use checks whereas a single-use endoscope does not need pre-use reprocessing results in reduced usability.

Embodiments described below can provide an endoscope holder capable of improving usability during pre-use checks.

Embodiments of the present invention will be described below with reference to the drawings. However, the present invention is not limited by the embodiment described below.

Note that in the drawings, the same or corresponding elements are denoted by the same reference signs as appropriate. It should also be noted that the drawings are schematic and that in a single drawing, length relationships among different elements, length ratios among different elements, or quantities of multiple elements may not be shown in their true relationships to one another for simplicity of explanation. Furthermore, length relationships or length ratios among different elements may not coincide with one another among different drawings.

First Embodiment

FIGS. 1 to 9 show a first embodiment of the present invention. FIG. 1 is a perspective view showing a configuration of an endoscope system according to the first embodiment.

As shown in FIG. 1, an endoscope system 1 includes an endoscope 2, a light source device 3, a video processor 4, a suction pump 5, a water feeding tank 6, and a monitor 7.

The light source device 3, the video processor 4, the suction pump 5, the water feeding tank 6, and the monitor 7 are mounted on or fixed to an endoscope system cart 8. Before use, the endoscope 2 can undergo pre-use checks and the like by being hung on an endoscope holder 10 attached to an upper end portion of a scope pole 9 of an endoscope system cart 8. Note that the endoscope system cart 8 is also called a trolley. The endoscope holder 10 is also called a scope hunger. The scope pole 9 has been installed on the endoscope system cart 8 in advance.

The endoscope 2 according to the present embodiment is configured, for example, as a single-use endoscope discarded after a single use. The endoscope 2 includes an insertion portion 21, an operation portion 22, and a universal cable 23.

The insertion portion 21 is a part inserted into a subject. The insertion portion 21 includes a distal end portion 21*a*, a bending portion 21*b*, and a flexible tubular portion 21*c* in order from a distal end side to a proximal end side.

An objective optical system, an illumination optical system, an image sensor, a distal end side opening of a treatment instrument channel, and the like are provided in the distal end portion 21*a*. The treatment instrument channel may combine, for example, a suction channel.

The bending portion 21*b* is a bendable part disposed on the proximal end side of the distal end portion 21*a*. When a bending operation knob 22*b* described later is operated, the bending portion 21*b* is bent, for example, in four directions of up, down, left, and right.

The flexible tubular portion 21*c* is a tubular portion having flexibility and disposed on the proximal end side of the bending portion 21*b*. Note that a case in which the endoscope 2 is a flexible endoscope provided with the flexible tubular portion 21*c* is taken as an example herein. However, the endoscope 2 may be a rigid endoscope having a rigid portion corresponding to the flexible tubular portion 21*c*.

The operation portion 22 is disposed on the proximal end side of the insertion portion 21 and includes a grasping portion 22*a*, the bending operation knob 22*b*, operation buttons 22*c*, and a treatment instrument insertion port 22*d*.

The grasping portion 22*a* is used by an operator to grasp the endoscope 2 with his/her palm.

The bending operation knob 22*b* is an operation device used to perform an operation of bending the bending portion 21*b* using, for example, the thumb of a hand grasping the grasping portion 22*a*. When the bending operation knob 22*b* is operated, the bending wires are pulled bending the bending portion 21*b*.

The operation buttons 22*c* are operation devices used to perform various operations of the endoscope 2, including image pickup, suction, air/water feeding, and the like.

The treatment instrument insertion port 22*d* is a proximal end side opening of the treatment instrument channel. A treatment instrument is inserted into the treatment instrument channel through the treatment instrument insertion port 22*d*.

The universal cable 23 is extended, for example, from a flank of the operation portion 22. A tapered bend stopper 23*a* is provided on the proximal end side of the universal cable 23 extended from the operation portion 22. A connector 23*b* for use to connect to the light source device 3 and the video processor 4 is provided on an extending end of the universal cable 23. The connector 23*b* divides into two branches, one of which is connected to the light source device 3 and the other is connected to the video processor 4.

The light source device 3 supplies illuminating light to the endoscope 2. The light source device 3 includes, for example, a white light source and may include a special light source, as required, to conduct fluorescence observation, NBI (narrow band imaging), or the like. The light source device 3 is not limited to being constructed separately from the video processor 4, but may be constructed integrally with the video processor 4.

The video processor 4 receives an image pickup signal from the endoscope 2, applies various image processing to the image pickup signal, and generates a displayable image signal. The video processor 4 may superimpose various types of information such as character information or guide information on the image signal.

Note that the video processor 4 may be configured to achieve functions of various components when an ASIC (application specific integrated circuit) including a CPU (central processing unit) and the like or a processor such as an FPGA (field programmable gate array) reads and executes processing programs stored in a storage device such as a memory (or a recording medium). At least part of the video processor 4 may be configured as a dedicated electronic circuit.

The image signal generated by the video processor 4 is outputted to the monitor 7. The monitor 7, which is a display device, receives the image signal from the video processor 4 and displays an endoscopic image.

The suction pump 5 performs suction out of the subject via the treatment instrument channel, which combines, for example, a suction channel. Suction is performed out of the subject when a suction button among the operation buttons 22*c* is operated.

The water feeding tank 6 reserves saline or the like to be fed into the subject. The light source device 3 is provided with a non-illustrated air feeding pump, and when an air/water feeding button among the operation buttons 22*c* is set to Air, air is fed into the subject. When the air/water feeding button among the operation buttons 22*c* is set to Water, the air feeding pump feeds air toward the water feeding tank 6, which then feeds water into the subject from the water feeding tank 6 under the pressure of the fed air.

Figure 2:
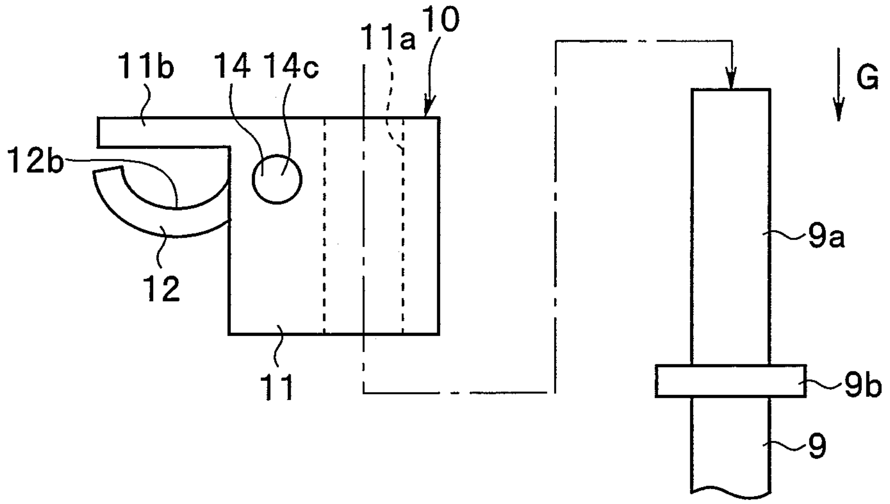
FIG. 2 is a side view showing how an endoscope holder according to the first embodiment is attached to a scope pole of an endoscope system cart.
Figure 3:
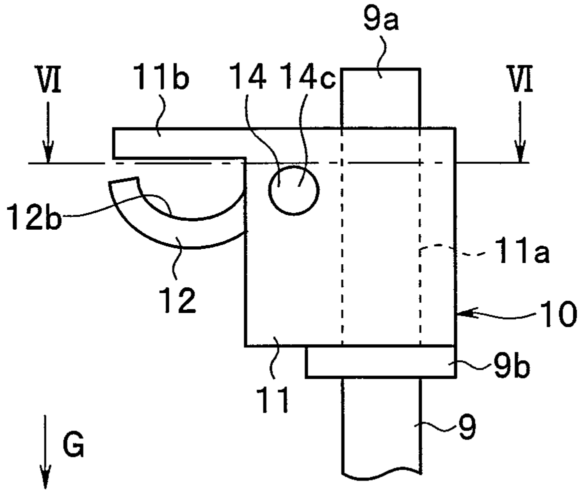
FIG. 3 is a side view showing the endoscope holder attached to the scope pole in the first embodiment.

FIG. 2 is a side view showing how the endoscope holder 10 according to the first embodiment is attached to the scope pole 9 of the endoscope system cart 8. FIG. 3 is a side view showing the endoscope holder 10 attached to the scope pole 9 in the first embodiment.

A holder insertion portion 9*a* and a flange 9*b* are provided on the upper end portion of the scope pole 9, where the endoscope holder 10 is attached to the holder insertion portion 9*a*.

The endoscope holder 10 includes a holder body 11. The holder body 11 includes an attachably-shaped portion 11*a* attachable to the scope pole 9 of the endoscope system cart 8. The attachably-shaped portion 11*a* according to the present embodiment is a pass-through hole inserted around the holder insertion portion 9*a*. However, the attachably-shaped portion 11*a* is not limited to a pass-through hole, and may have another form.

The endoscope holder 10 may be a single-use type discarded after a single use. In that case, the endoscope holder 10 is shipped under sterile conditions by being sealed in a sterile pack. Note that if the endoscope 2 and the endoscope holder 10 are a single-use type discarded after a single use, the endoscope holder 10 may be shipped by being sealed in the same sterile pack as the endoscope 2. In that case, the endoscope 2 and the endoscope holder 10 may be sealed in the same sterile pack with the endoscope 2 being held in the endoscope holder 10.

In the case of the single-use endoscope holder 10, the sterile pack is opened and the endoscope holder 10 is attached to the holder insertion portion 9*a* at the time of use. The single-use endoscope holder 10 is removed from the holder insertion portion 9*a* and discarded after a single use. Thus, the endoscope holder 10 is removable from the scope pole 9.

In inserting the attachably-shaped portion 11*a* around the holder insertion portion 9*a*, when a bottom face of the holder body 11 hits the flange 9*b*, position of the endoscope holder 10 in the direction of gravity G is defined by the flange 9*b* as shown in FIG. 3.

Figure 4:
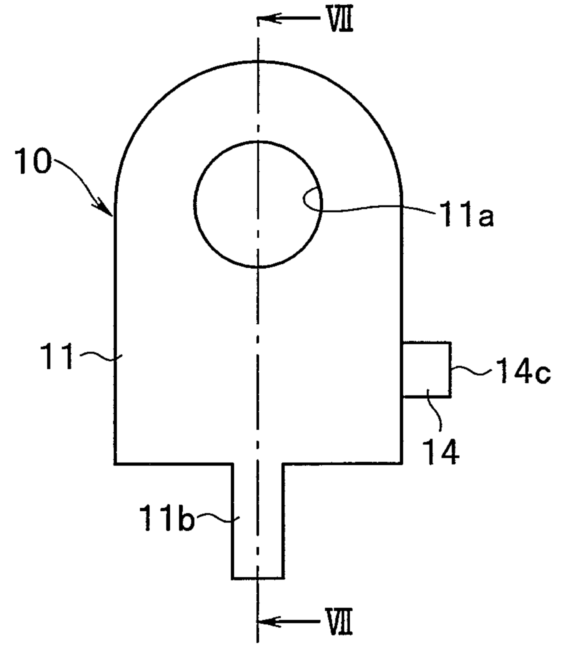
FIG. 4 is a plan view showing the endoscope holder according to the first embodiment.
Figure 5:
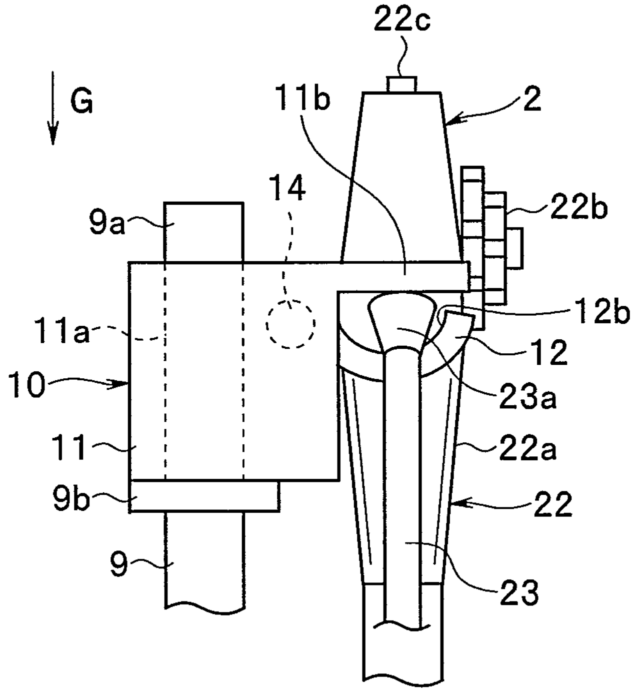
FIG. 5 is a diagram showing how an endoscope is hung on the endoscope holder according to the first embodiment.
Figure 6:
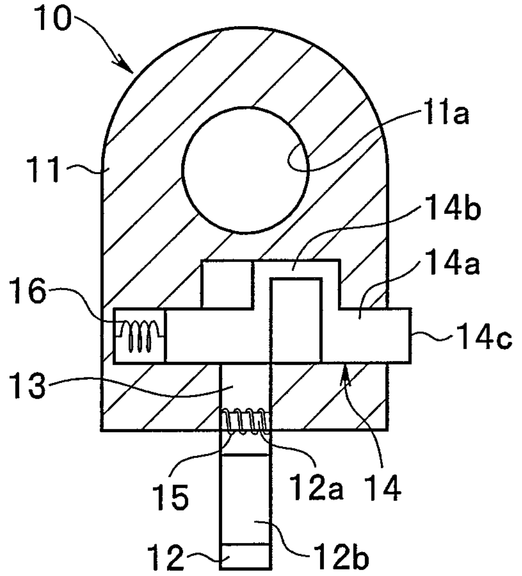
FIG. 6 is a sectional view of the endoscope holder taken along line VI-VI in FIG. 3 when a slide member is at a first position in the first embodiment.
Figure 7:
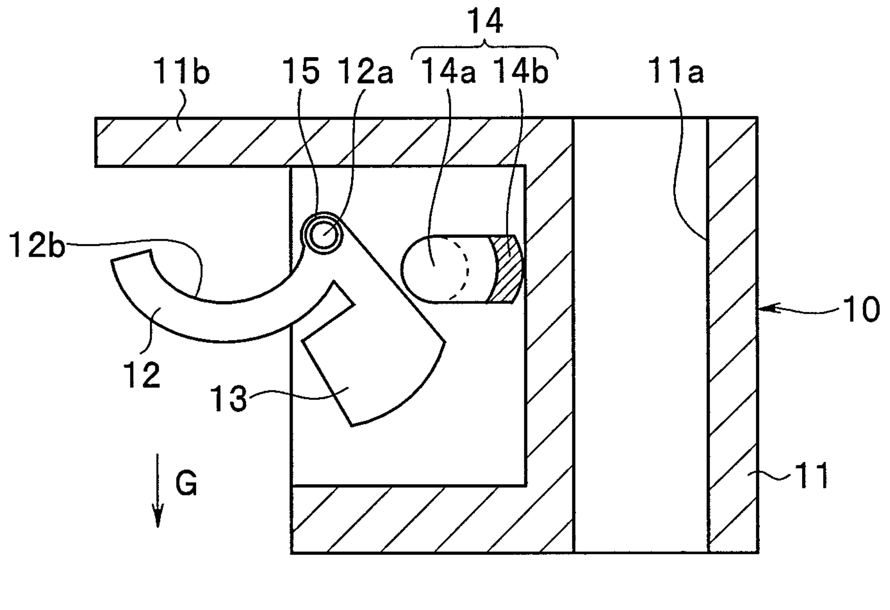
FIG. 7 is a sectional view of the endoscope holder taken along line VII-VII in FIG. 4 when the slide member is at the first position in the first embodiment.

FIG. 4 is a plan view showing the endoscope holder 10 according to the first embodiment. FIG. 5 is a diagram showing how the endoscope 2 is hung on the endoscope holder 10 according to the first embodiment. FIG. 6 is a sectional view of the endoscope holder 10 taken along line VI-VI in FIG. 3 when a slide member 14 is at a first position in the first embodiment. FIG. 7 is a sectional view of the endoscope holder 10 taken along line VII-VII in FIG. 4 when the slide member 14 is at the first position in the first embodiment.

The endoscope holder 10 further includes a hanger 12, a support frame 13, the slide member 14, a first urging member (first biasing member) 15, and a second urging member (second biasing member) 16.

Figure 8:
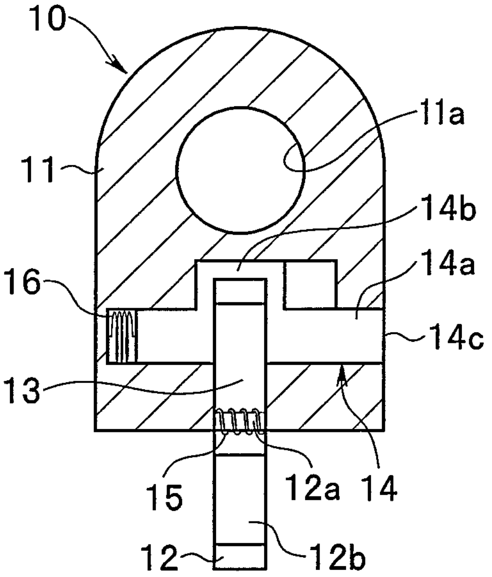
FIG. 8 is a sectional plan view of the endoscope holder when the slide member is at a second position in the first embodiment.
Figure 9:
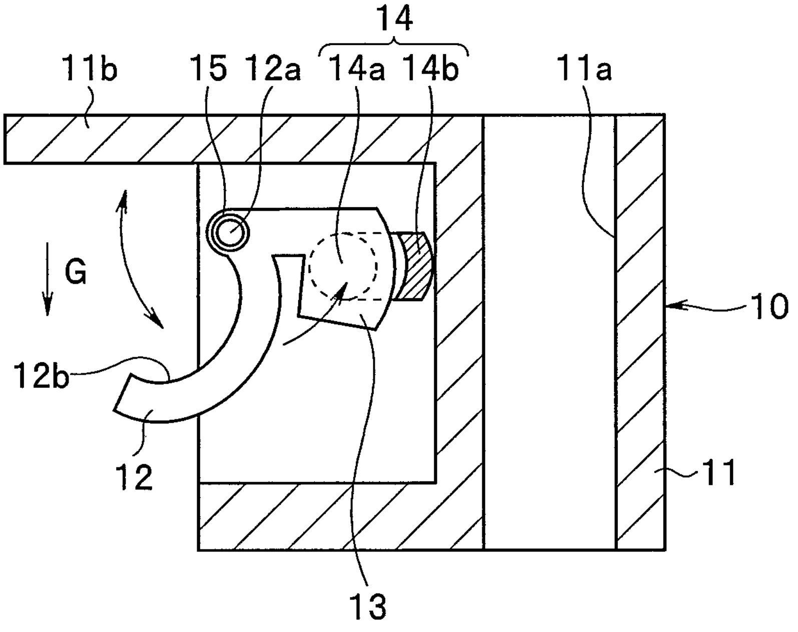
FIG. 9 is a longitudinal sectional view of the endoscope holder when the slide member is at the second position in the first embodiment.

The hanger 12 is pivotably attached to the holder body 11 so as to be pivotable around a pivot axis 12*a* at a first angle (a first angle position) and a second angle (a second angle position). FIGS. 2 to 7 show states in which the hanger 12 is at the first angle. FIGS. 8 and 9 described later show states in which the hanger 12 is at the second angle.

The hanger 12 is a part on which the endoscope 2 is hung. The hanger 12 is, for example, hook-shaped (arc-shaped) and is provided with a concave-shaped portion 12*b* configured to prevent the endoscope 2 from slipping off the hanger 12 by gravity when the hanger 12 is at the first angle.

The first angle is an angle of 90 degrees with respect to the direction of gravity G as an example. However, the first angle is not limited to this example, and the angle may be set such that the endoscope 2 will not slip off the hanger 12 by gravity.

Note that whereas the hanger 12 provided with the concave-shaped portion 12*b* has been described here by way of example, as long as the endoscope 2 placed at the first angle will not slip off the hanger 12, it is all right even if that surface of the hanger 12 on which the endoscope 2 is hung is flat (i.e., even if the concave-shaped portion 12*b* is not provided).

Even if the entire hanger 12 is not hook-shaped, the surface on which the endoscope 2 is hung may be flat as a whole and a concave-shaped portion is provided in part of the flat surface.

As shown in FIG. 5, for example, the bend stopper 23*a* on the proximal end side of the universal cable 23 of the endoscope 2 is hung on the hanger 12.

On the holder body 11, an opposing member (plate) 11*b* is provided opposite the hanger 12 placed at the first angle. The opposing member 11*b* may be provided either integrally with the holder body 11 or may be fixed by providing separately from the holder body 11. However, the present disclosure is not limited to a configuration in which the opposing member 11*b* is provided, and a configuration in which the opposing member 11*b* is not provided on the holder body 11 may be adopted.

The support frame 13 pivots integrally with the hanger 12 around the pivot axis 12*a*. The support frame 13 extends in a direction different from the hanger 12 as viewed from the pivot axis 12*a* of the hanger 12. The hanger 12 and the support frame 13 may be configured as a first arm and second arm of a single lever member. Alternatively, the hanger 12 and the support frame 13 may be produced as separate members and then combined together so as to pivot integrally.

The slide member 14 is supported by the holder body 11 in such a way as to be slidable to the first position and the second position. FIGS. 2 to 7 show states in which the slide member 14 is at the first position. FIGS. 8 and 9 described later show states in which the slide member 14 is at the second position.

The slide member 14 includes a slide body 14*a*, a concave-shaped portion (concave portion) 14*b*, and a button 14*c*. The slide body 14*a* is configured, for example, as a columnar member and is slidable in a direction parallel to the pivot axis 12*a*.

The concave-shaped portion 14*b* is provided in part of the slide body 14*a* in a sliding direction. More specifically, the concave-shaped portion 14*b* is provided at a position opposite the support frame 13 in a direction orthogonal to the sliding direction when the slide member 14 is at the second position.

The button 14*c* is provided on one end side of the slide member 14. When the slide member 14 is at the first position, the button 14*c* protrudes outward from the holder body 11, allowing a user to press the button 14*c* with a finger or the like. When the button 14*c* is pressed, the slide member 14 slides integrally with the button 14*c*.

The button 14*c* may be provided integrally with the slide body 14*a*. Alternatively, the button 14*c* may be provided separately from the slide body 14*a* and attached to the slide body 14*a* so as to slide integrally with the slide body 14*a*.

The first urging member 15 urges the hanger 12 from the first angle such as shown in FIG. 7 toward the second angle such as shown in FIG. 9. The first urging member 15 is configured, for example, as a torsion spring.

FIG. 8 is a sectional plan view of the endoscope holder 10 when the slide member 14 is at the second position in the first embodiment. FIG. 9 is a longitudinal sectional view of the endoscope holder 10 when the slide member 14 is at the second position in the first embodiment.

The second urging member 16 urges the slide member 14 from the second position such as shown in FIG. 8 toward the first position such as shown in FIG. 6. The second urging member 16 is configured, for example, as a compression coil spring.

When the slide member 14 is at the first position such as shown in FIG. 6, the support frame 13 hits the slide body 14*a*, restricting the support frame 13 and the hanger 12 from pivoting as shown in FIG. 7. In other words, at the first position, the slide member 14 restricts the hanger 12 placed at the first angle from pivoting to the second angle and thereby keeps the hanger 12 at the first angle.

As shown in FIG. 5, the hanger 12 and the opposing member 11*b* sandwich the bend stopper 23*a* on the proximal end side of the universal cable 23. Thus, when the slide member 14 is at the first position and the hanger 12 is kept at the first angle, the opposing member 11*b* restricts removal of the endoscope 2 hung on the hanger 12. Unless the button 14*c* is pressed, the endoscope 2 cannot be removed from the endoscope holder 10.

When the slide member 14 is at the second position such as shown in FIG. 8, the support frame 13 does not hit the slide body 14*a* as shown in FIG. 9 and thereby the slide member 14 permits the support frame 13 to pivot. In other words, when the slide member 14 is at the second position, the concave-shaped portion 14*b* opposes the support frame 13 bypassing a pivot path of the support frame 13 and thereby permits the support frame 13 and the hanger 12 to pivot. Because the concave-shaped portion 14*b* is outside a pivot range of the support frame 13, the support frame 13 can enter the concave-shaped portion 14*b* without being restricted from pivoting by the concave-shaped portion 14*b*. In this way, at the second position, the slide member 14 permits the hanger 12 to pivot from the first angle to the second angle.

As the button 14*c* is pressed against an urging force of the second urging member 16 with any timing, the hanger 12 is directed to pivot and the slide member 14 slides from the first position to the second position. When the slide member 14 reaches the second position, the hanger 12 is permitted to pivot, and pivots from the first angle to the second angle under an urging force of the first urging member 15. When the hanger 12 opens to the second angle, the user can remove the endoscope 2 from the endoscope holder 10. Thus, the button 14*c* functions as a scope removal button that can be operated with any timing.

Note that when the endoscope holder 10 is attached to the scope pole 9 of the endoscope system cart 8, the pivot axis 12*a* of the hanger 12 is placed so as to intersect the direction of gravity G (e.g., orthogonally intersect the direction of gravity G). In this state, gravity acting on the hanger 12 pivots the hanger 12 from the first angle toward the second angle. On the other hand, gravity acting on the support frame 13 acts to pivot the support frame 13 in a direction opposite the direction in which the hanger 12 is caused to pivot by gravity.

Thus, lengths of the hanger 12 and the support frame 13 from the pivot axis 12*a* as well as weight balance between the hanger 12 and the support frame 13 may be adjusted such that moment of force acting on the hanger 12 by gravity will be larger than moment of force acting on the support frame 13 by gravity. Consequently, when the slide member 14 is slid from the first position to the second position, the hanger 12 pivots toward the second angle by gravity. In this case, the first urging member 15 does not have to be provided.

The support frame 13 and the slide member 14 may be configured, for example, to be coupled via a cam. In that case, it is advisable to configure the endoscope holder such that as the slide member 14 slides from the first position to the second position, the support frame 13 will pivot due to cam coupling, eventually causing the hanger 12 to pivot from the first angle to the second angle. If this configuration is adopted, there is no need to provide the first urging member 15.

The endoscope 2 can be hung on the hanger 12 placed at the first angle as shown in FIG. 5. On the other hand, when the hanger 12 is at the second angle as shown in FIG. 9, the endoscope 2 comes off the hanger 12 by gravity. Thus, the endoscope 2 cannot be hung on the hanger 12 placed at the second angle.

Regarding the second angle, the endoscope 2 may come off the hanger 12 by gravity and cannot be hung. A specific angle is a value corresponding to the length of the hanger 12 from the pivot axis 12*a*, a curved shape of the concave-shaped portion 12*b*, and the like and it is difficult to give numerical examples, but an angle of 0 to 30 degrees with respect to the direction of gravity G can be cited tentatively.

The endoscope 2 can be set up on the endoscope system cart 8 as follows.

As described above, when the endoscope holder 10 is sealed in the sterile pack by holding the endoscope 2, once the sterile pack is opened and the endoscope holder 10 holding the endoscope 2 is attached to the holder insertion portion 9*a*, the endoscope 2 becomes held to the endoscope system cart 8.

If the endoscope holder 10 is sealed singly in a sterile pack, the sterile pack is opened and the endoscope holder 10 is taken out of the sterile pack. Then the endoscope holder 10 is attached to the holder insertion portion 9*a*.

In putting the endoscope holder 10 singly into the sterile pack, from the viewpoint of further improving usability, the sterile pack may be sealed with the hanger 12 being at the second angle (i.e., with the hanger 12 being open to the opposing member 11*b*). However, if the hanger 12 is at the first angle, the hanger 12 is placed at the second angle by sliding the slide member 14 from the first position to the second position.

With the hanger 12 being open at the second angle, the user sets the endoscope 2 on the hanger 12 and manually closes the hanger 12 to the first angle. Consequently, the support frame 13 comes off the concave-shaped portion 14*b* of the slide member 14 and the slide member 14 moves from the second position to the first position under the urging force of the second urging member 16.

Then, even if the user does not hold the hanger 12 manually, the support frame 13 hits the slide body 14*a*, holding the hanger 12 at the first angle. Consequently, the endoscope 2 is kept being held to the endoscope system cart 8.

According to the first embodiment, when the hanger 12 is at the first angle, the opposing member 11*b* restricts removal of the endoscope 2 hung on the hanger 12. This makes it possible to prevent the endoscope 2 from inadvertently falling off the endoscope holder 10.

When using the endoscope 2, the user presses the button 14*c* to direct the hanger 12 to pivot. This makes it possible to proactively prevent the endoscope 2 from being enabled when the user does not have an intention to use the endoscope 2.

After the endoscope 2 is removed from the endoscope holder 10 by a press of the button 14*c*, the hanger 12 is kept at the second angle under the urging force of the first urging member 15 unless operated intentionally. Then, even if an attempt is made to pull back the button 14*c* from the depressed position, the button 14*c* cannot be returned to the position before the press with the slide body 14*a* hitting the support frame 13.

In this way, once the button 14*c* is pressed, the endoscope holder 10 becomes basically non-reusable, preventing the used endoscope 2 from being hung on the endoscope holder 10 by mistake. Since erroneous reuse of the endoscope holder 10 can be prevented, it is possible to prevent a sterilized new endoscope 2 from causing cross infection via the endoscope holder 10. Since a used endoscope 2 is never hung on the endoscope holder 10, cross infection via the scope pole 9 or the endoscope system cart 8 can also be prevented.

Furthermore, if the endoscope holder 10 is a single-use type, a reprocessing process of the endoscope holder 10 may be eliminated, and cross infection of the endoscope 2 via the endoscope holder 10 can be prevented more reliably.

First Modification of First Embodiment

Figure 10:
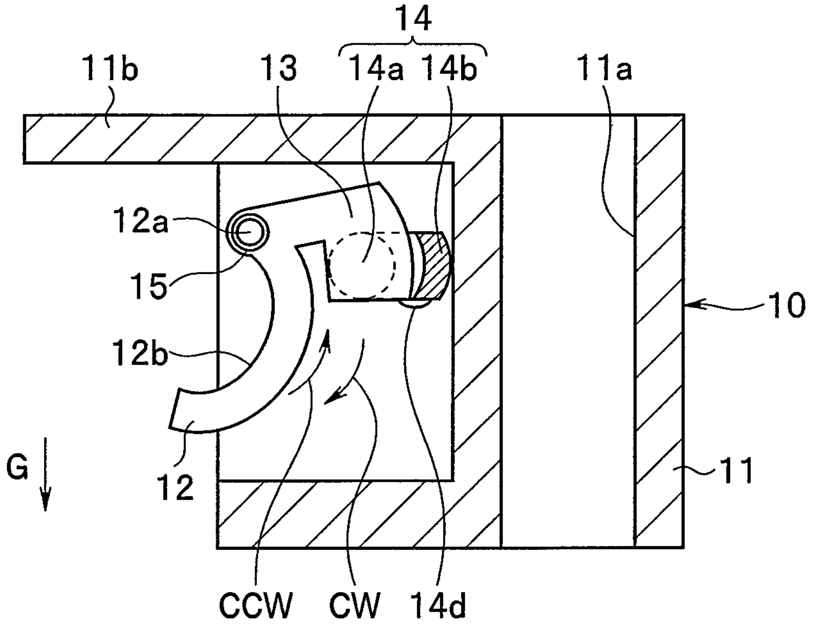
FIG. 10 is a longitudinal sectional view of the endoscope holder in which the slide member is provided with a pawl configured to restrict pivoting of a hanger by being engaged with a support frame in a first modification of the first embodiment.

FIG. 10 is a longitudinal sectional view of the endoscope holder 10 in which the slide member 14 is provided with a pawl 14*d* configured to restrict pivoting of the hanger 12 by being engaged with the support frame 13 in a first modification of the first embodiment.

In the first modification, the same components as in the first embodiment are denoted by the same reference signs, and description thereof will be omitted as appropriate. In the first modification, differences from the first embodiment will be described mainly.

The slide member 14 further includes the pawl 14*d* protruding from the concave-shaped portion 14*b* toward the pivot path of the support frame 13.

When the hanger 12 pivots from the first angle to the second angle, the pawl 14*d* permits the support frame 13 to pass the pawl 14*d* by pivoting in a counterclockwise direction CCW in FIG. 10.

On the other hand, when the hanger 12 is at the second angle, the pawl 14*d* engages with the support frame 13 and thereby restricts the support frame 13 from passing the pawl 14*d* by pivoting in a clockwise direction CW in FIG. 10. Consequently, the pawl 14*d* restricts the hanger 12 pivoting integrally with the support frame 13 from pivoting from the second angle toward the first angle. In this way, the pawl 14*d* makes up a lock mechanism that makes the endoscope holder 10 non-reusable when the button 14*c* is pressed once.

According to the first modification of the first embodiment, since the hanger 12 cannot be returned to the first angle even if pulled, the endoscope holder 10 can be inhibited more reliably from being reused after the button 14*c* is pressed once.

Second Modification of First Embodiment

Figure 11:
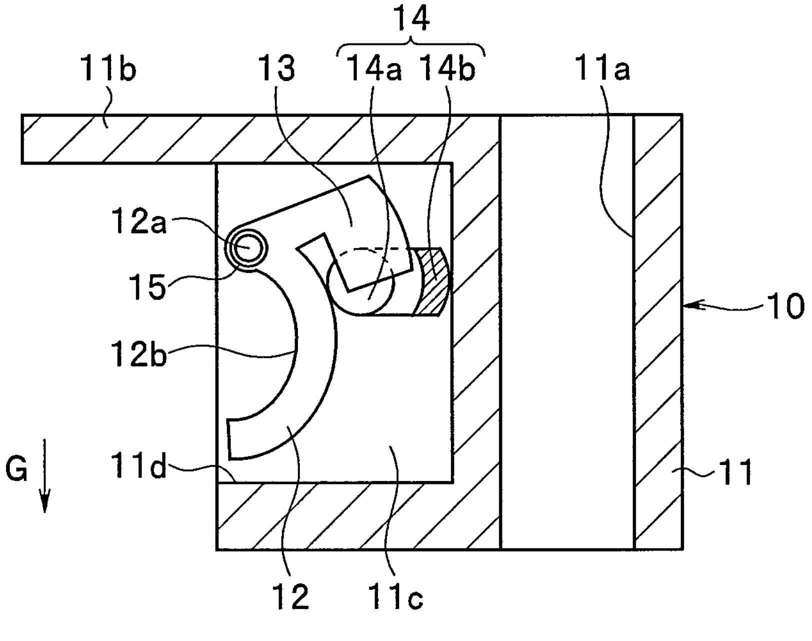
FIG. 11 is a longitudinal sectional view of the endoscope holder, the entire hanger of which is housed in a housing when the slide member is at the second position in a second modification of the first embodiment.

FIG. 11 is a longitudinal sectional view of the endoscope holder 10, the entire hanger 12 of which is housed in a housing 11*c* when the slide member 14 is at the second position in a second modification of the first embodiment.

In the second modification, the same components as in the first embodiment are denoted by the same reference signs, and description thereof will be omitted as appropriate. In the second modification, differences from the first embodiment will be described mainly.

The holder body 11 includes an opening 11*d* provided on a pivot path of the hanger 12 and the housing 11*c* provided inside the opening 11*d*. The opening 11*d* is configured with a width that does not allow the user to insert a finger.

When the slide member 14 slides from the first position to the second position, the hanger 12 enters the housing 11*c* through the opening 11*d*. When the slide member 14 is at the second position, the entire hanger 12 is housed in the housing 11*c*.

According to the second modification of the first embodiment, when the button 14*c* is pressed once, the entire hanger 12 is housed in the housing 11*c*. Therefore, the user cannot return the hanger 12 to the first angle by pulling the hanger 12 by hand. Thus, the endoscope holder 10 can be inhibited from being reused after the button 14*c* is pressed once.

Note that the endoscope holder 10 may be inhibited more reliably from being reused by adding the pawl 14*d* described in the first modification of the first embodiment to the configuration of the second modification of the first embodiment.

Second Embodiment

Figure 12:
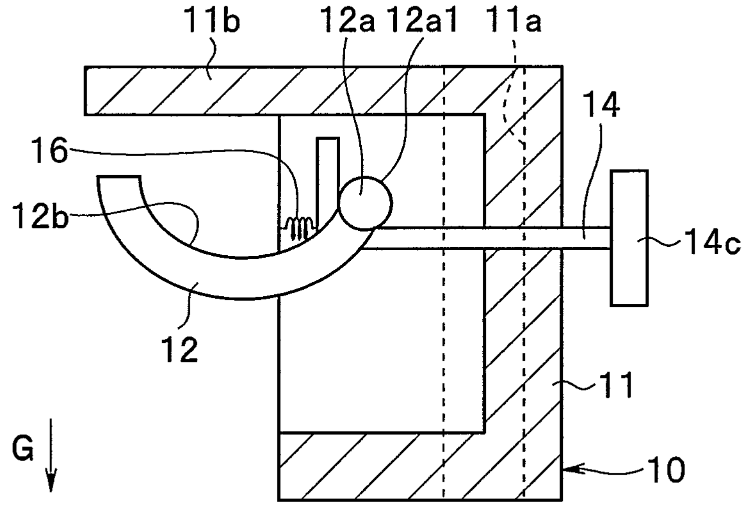
FIG. 12 is a longitudinal sectional view showing a configuration of an endoscope holder in a second embodiment of the present disclosure.
Figure 13:
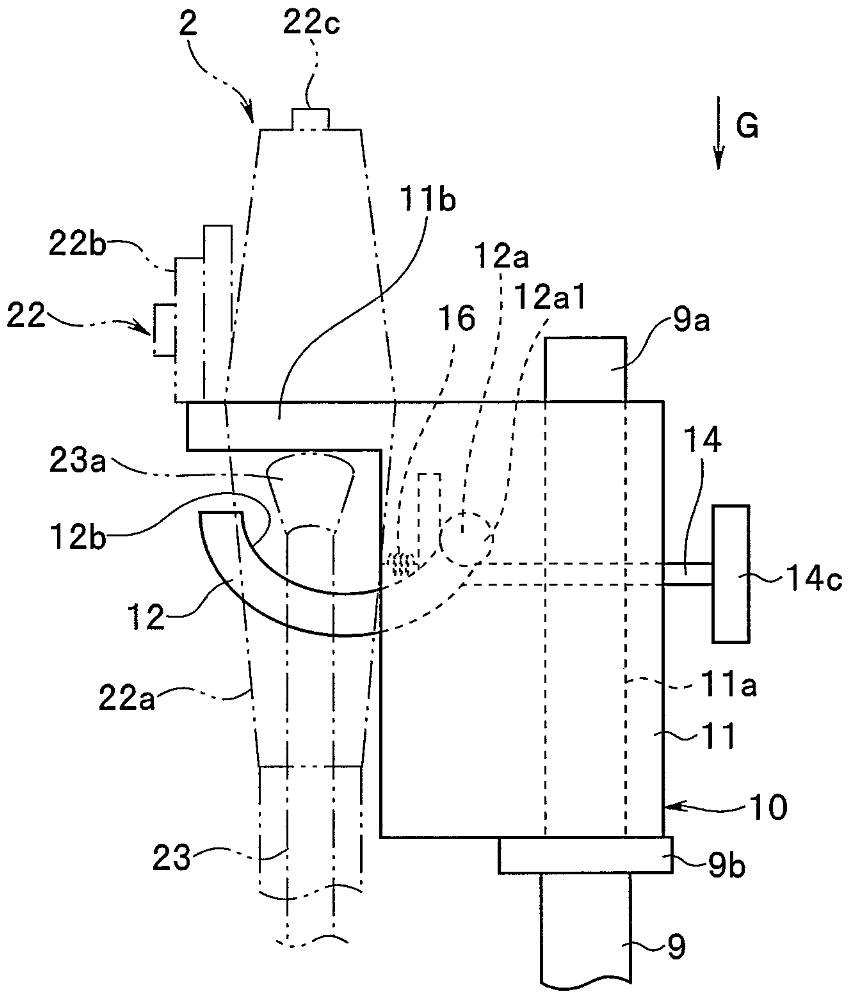
FIG. 13 is a diagram showing how an endoscope is hung on the endoscope holder according to the second embodiment.
Figure 14:
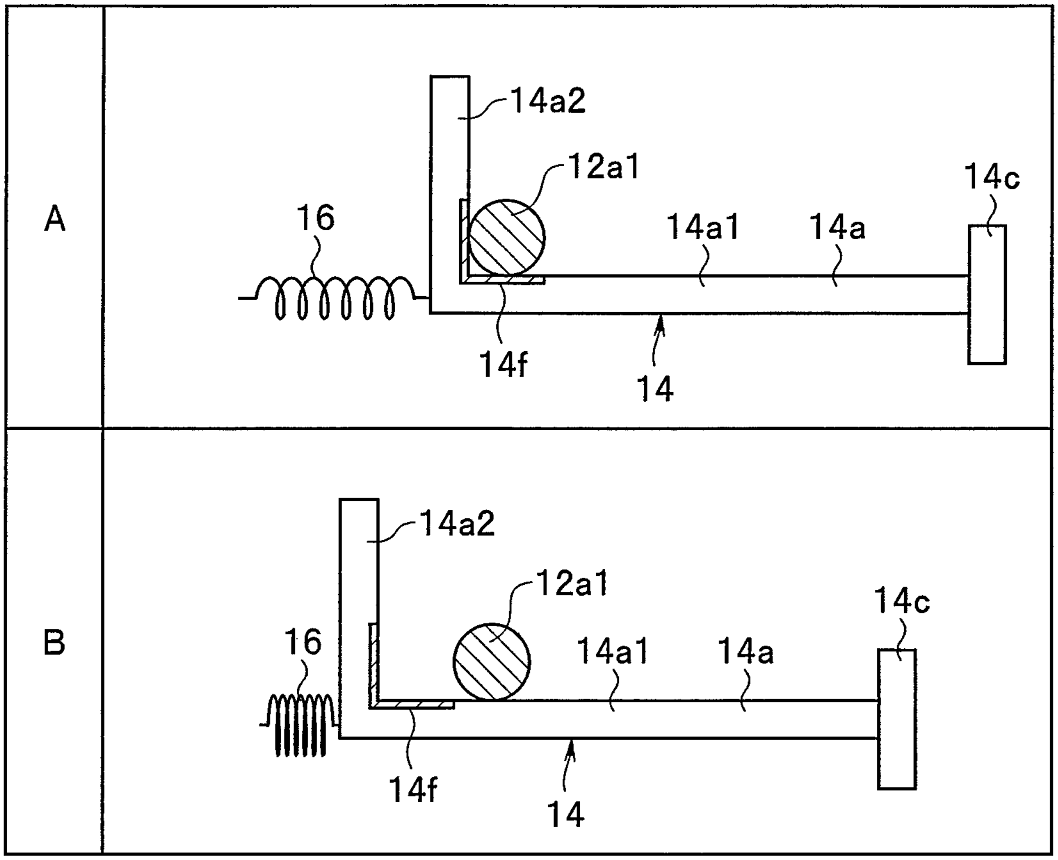
FIG. 14 is a chart showing a relationship between high-friction surfaces and an axial member on the endoscope holder according to the second embodiment, where the high-friction surfaces are provided on the slide member.

FIGS. 12 to 14 show a second embodiment of the present disclosure. FIG. 12 is a longitudinal sectional view showing a configuration of an endoscope holder 10 in the second embodiment. FIG. 13 is a diagram showing how the endoscope 2 is hung on the endoscope holder 10 according to the second embodiment. FIG. 14 is a chart showing a relationship between high-friction surfaces 14*f* and an axial member 12*a*1 on the endoscope holder 10 according to the second embodiment, where the high-friction surfaces 14*f* are provided on the slide member 14.

In the second embodiment, the same components as in the first embodiment are denoted by the same reference signs, and description thereof will be omitted as appropriate. In the second embodiment, differences from the first embodiment will be described mainly.

As shown in FIG. 12, the endoscope holder 10 according to the present embodiment does not include the support frame 13 and the hanger 12 is an arm configured to pivot around the pivot axis 12*a*.

As shown in FIG. 13, the present embodiment is similar to the first embodiment in that the bend stopper 23*a* of the endoscope 2 is hung on the hanger 12 and the bend stopper 23*a* is sandwiched between the hanger 12 and the opposing member 11*b*.

The endoscope holder 10 includes the axial member 12*al* serving as the pivot axis 12*a* of the hanger 12. The axial member 12*al* is provided so as to pivot integrally with the hanger 12. The axial member 12*al* may be provided integrally with the hanger 12 or may be provided separately and fixed to the hanger 12 so as to pivot integrally.

The pivot axis 12*a* according to the first embodiment may be configured as the axial member 12*al* or may be configured, for example, as projections protruding to both sides from the proximal end side of the hanger 12. In contrast, the pivot axis 12*a* according to the present embodiment is configured, for example, as the axial member 12*al* circularly cylindrical in shape.

The slide member 14 according to the present embodiment is slidable, for example, in a direction orthogonal to the pivot axis 12*a*. Thus, the second urging member 16 is also placed so as to urge the slide member 14 in the direction orthogonal to the pivot axis 12*a*.

More specifically, the second urging member 16 urges the slide member 14 from the second position such as shown in Section B of FIG. 14 toward the first position such as shown in Section A of FIG. 14. Furthermore, the second urging member 16 presses and thereby urges the slide member 14 located at the first position toward the axial member 12*a*1.

The slide body 14*a* includes a first body 14*al* and a second body 14*a*2. The first body 14*al* extends from the button 14*c* in the sliding direction. The second body 14*a*2 extends from the first body 14*al* in a direction intersecting (e.g., orthogonally intersecting) both the sliding direction and an axial direction of the pivot axis 12*a*.

The slide member 14 is further provided with the high-friction surfaces 14*f*. The high-friction surfaces 14*f* are provided, for example, on surfaces facing the axial member 12*al* at a corner where the first body 14*al* and the second body 14*a*2 are connected. Note that surfaces of the slide member 14 other than the high-friction surfaces 14*f* are, for example, smooth surfaces with low friction.

As shown in Section A of FIG. 14, when the slide member 14 is at the first position, the high-friction surfaces 14*f* are in contact with the axial member 12*a*1. When the slide member 14 is at the first position, the second urging member 16 urges the high-friction surfaces 14*f* toward the axial member 12*a*1. The high-friction surfaces 14*f* generate frictional forces against the axial member 12*a*1, restricting the pivoting of the axial member 12*al* and hanger 12.

As shown in Section B of FIG. 14, when the slide member 14 is at the second position, the high-friction surfaces 14*f* are out of contact with the axial member 12*a*1. When the slide member 14 is at the second position, the high-friction surfaces 14*f* do not generate frictional forces against the axial member 12*a*1, and thereby permit the axial member 12*al* and the hanger 12 to pivot.

The second embodiment provides advantages approximately similar to the advantages of the first embodiment described earlier. Even if the support frame 13 is not provided, using, for example, frictional forces between the axial member 12*al* of the hanger 12 and the slide member 14, the second embodiment can implement a configuration in which the hanger 12 does not pivot and the endoscope 2 does not become usable unless the button 14*c* is pressed.

Modification of First and Second Embodiments

Figure 15:
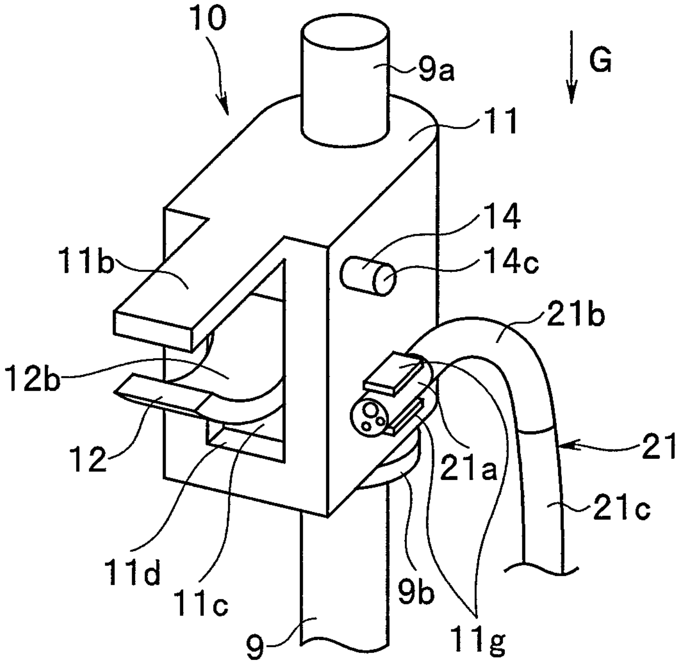
FIG. 15 is a perspective view showing an endoscope holder provided with a gripper-shaped portion configured to hold a distal end portion of an insertion portion of an endoscope in a modification of the first and second embodiments.
Figure 16:
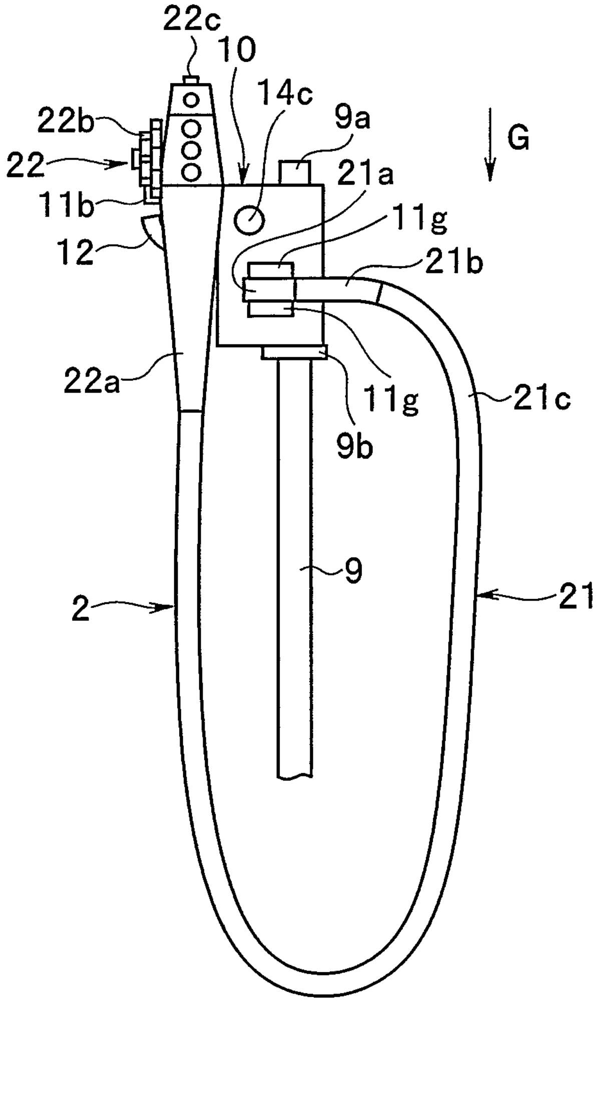
FIG. 16 is a side view showing how the distal end portion of the insertion portion of the endoscope is held by the gripper-shaped portion provided on the endoscope holder according to the modification of the first and second embodiments.

FIGS. 15 and 16 show a modification applicable to the first and second embodiments. FIG. 15 is a perspective view showing an endoscope holder 10 provided with a gripper-shaped portion (fixture) 11*g* configured to releasably hold the distal end portion 21*a* of the insertion portion 21 of the endoscope 2 in a modification of the first and second embodiments. FIG. 16 is a side view showing how the distal end portion 21*a* of the insertion portion 21 of the endoscope 2 is held by the gripper-shaped portion 11*g* provided on the endoscope holder 10 according to the modification of the first and second embodiments.

In the present modification, the same components as in the first and second embodiments are denoted by the same reference signs, and description thereof will be omitted as appropriate. In the present modification, differences from the first and second embodiments will be described mainly.

The holder body 11 of the endoscope holder 10 further includes the gripper-shaped portion 11*g* configured to hold the distal end portion 21*a* of the insertion portion 21 of the endoscope 2.

In the example shown in FIGS. 15 and 16, the gripper-shaped portion 11*g* is provided on a flank of the holder body 11, i.e., for example, a flank from which the button 14*c* protrudes. The gripper-shaped portion 11*g* is made up, for example, of a pair of projections configured to sandwich and hold the distal end portion 21*a*.

However, the gripper-shaped portion 11*g* is not limited to a configuration made up of a pair of projections, and a hole that accepts insertion of the distal end portion 21*a* or another configuration may be adopted.

Note that if the endoscope 2 and the endoscope holder 10 are a single-use type discarded after a single use, the endoscope 2 and the endoscope holder 10 may be sealed in the same sterile pack with the endoscope 2 being held in the endoscope holder 10 and with the distal end portion 21*a* being held in the gripper-shaped portion 11*g*.

In that case, once the sterile pack is opened and the endoscope holder 10 holding the endoscope 2 is attached to the holder insertion portion 9*a*, the condition shown in FIG. 16 will result.

Then, the endoscope 2 can be used by removing the distal end portion 21*a* from the gripper-shaped portion 11*g* and pressing the button 14*c* once as with the above case.

According to the present modification, as the gripper-shaped portion 11*g* holds the distal end portion 21*a* by being sealed in a sterile pack, the distal end portion 21*a* can be protected when an unused endoscope 2 sealed in the sterile pack is shipped, transported, and the like.

Furthermore, after the sterile pack is opened, when the endoscope holder 10 and the endoscope 2 are being attached to the endoscope system cart 8, and even after being attached, the distal end portion 21*a* can be protected as long as the distal end portion 21*a* is being held in the gripper-shaped portion 11*g*. This makes it possible to prevent the distal end portion 21*a* from being damaged by contact with the endoscope system cart 8 or the like.

Since an objective optical system, an illumination optical system, an image sensor, and the like are provided in the distal end portion 21*a* as described above, as the distal end portion 21*a* is held in the gripper-shaped portion 11*g*, these damages can be prevented effectively.

Note that the present disclosure is not limited to the precise embodiments described above and may be embodied by changing components in the implementation stage without departing from the gist of the disclosure. Various aspects of the disclosure can be formed using appropriate combinations of the plurality of components disclosed in the above embodiments. For example, some of all the components disclosed in the embodiments may be deleted. Furthermore, components of different embodiments may be combined as appropriate. Thus, various alterations and applications are possible without departing from the gist of the disclosure.

What is claimed is:

1. An endoscope holder, comprising:
- a holder body;
- a hanger pivotably attached to the holder body to move between a first angle position and a second angle position; and
- a slide member supported on the holder body, the slide member configured to move slidably between a first position and a second position,
- wherein a pivot axis of the hanger is oriented in a direction intersecting a direction of gravity,
- wherein, at the first position, the slide member restricts pivoting of the hanger from the first angle position to the second angle position and, at the second position, the slide member permits pivoting of the hanger from the first angle position to the second angle position, and
- wherein, when the hanger is at the first angle position, the hanger is configured to support an endoscope by hanging the endoscope on the hanger and, when the hanger is at the second angle position, the hanger is configured to not support the endoscope by hanging.

2. The endoscope holder according to claim 1, further comprising a first biasing member,
- wherein, when the slide member is at the second position, the biasing member pivots the hanger toward the second angle position.

3. The endoscope holder according to claim 1, wherein, when the slide member is at the second position, gravity pivots the hanger toward the second angle position.

4. The endoscope holder according to claim 3, wherein a portion of the hanger is shaped to prevent the endoscope from disengaging from the hanger by gravity when the hanger is at the first angle position.

5. The endoscope holder according to claim 4, wherein the portion of the hanger has a concave shape.

6. The endoscope holder according to claim 1, further comprising a button configured to slide integrally with the slide member, wherein, when the button is in a pressed position, the slide member moves slidably between the first position to the second position to permit pivoting of the hanger from the first angle position to the second angle position.

7. The endoscope holder according to claim 1, wherein, when the slide member is at the first position and the hanger is located at the first angle position, a surface of the endoscope holder prevents removal of the endoscope hung on the hanger.

8. The endoscope holder according to claim 1, further comprising a second biasing member that biases the slide member from the second position toward the first position.

9. The endoscope holder according to claim 1, further comprising a support frame configured to pivot integrally with the hanger, wherein the support frame extends in a direction different from the hanger as viewed from a pivot axis of the hanger, wherein the support frame is restricted from pivoting by contacting the slide member when the slide member is at the first position, and wherein the support frame is permitted to pivot without contacting the slide member when the slide member is at the second position.

10. The endoscope holder according to claim 9, wherein:

the slide member includes a slide body having a recess, when the slide member is at the first position, the slide body is positioned in a pivot path of the support frame such that the support frame contacts the slide body when the hanger pivots from the first angle position to the second angle position, and when the slide member is at the second position, the recess of the slide body is positioned in the pivot path of the support frame.

11. The endoscope holder according to claim 10, wherein the slide body further comprises a pawl protruding from the concave-shaped portion toward the pivot path of the support frame, and wherein, when the slide member is at the second position and the hanger is at the second angle position, the pawl extends into the pivot path to contact the support frame to prevent pivoting of the support frame past the pawl when the hanger pivots toward the first angle position.

12. The endoscope holder according to claim 1, wherein:

the holder body includes a housing have an opening, when the slide member slides from the first position to the second position, the hanger enters the housing through the opening, and when the slide member is at the second position, an entirety of the hanger is located in the housing.

13. The endoscope holder according to claim 8, further comprising:

an axial member integral with the hanger; and a high-friction surface located on the slide member, wherein the axial member is a pivot axis of the hanger, wherein, when the slide member is at the first position, the second biasing member forces the high-friction surface toward the axial member and maintains a contact between the high-friction surface and the axial member, and wherein, when the slide member is at the second position, the high-friction surface does not contact the axial member.

14. The endoscope holder according to claim 13, wherein the contact between the high-friction surface and the axial member generates a frictional force restricting the axial member and the hanger from pivoting relative to each other.

15. The endoscope holder according to claim 1, wherein the holder body is configured to be attached to an endoscope system cart.

16. An endoscope holder, comprising:

a casing including a plate;

a hanger pivotably attached to the casing to move between a first angle position and a second angle position; and a slide member supported on the casing, the slide member configured to move slidably between a first position and a second position, wherein a pivot axis of the hanger is oriented in a direction intersecting a direction of gravity, wherein, at the first position, the slide member restricts pivoting of the hanger from the first angle position to the second angle position and, at the second position, the slide member permits pivoting of the hanger from the first angle position to the second angle position, and wherein, when the hanger is at the second angle position, the hanger is further from the plate than when the hanger is at the first angle position.

17. The endoscope holder according to claim 16, wherein the slide member includes:

a button exposed from the casing when the sliding member is at the first position;

a concave portion located in the casing; and a slide body located between the button and the concave portion.

18. The endoscope holder according to claim 17, further comprising a support frame connected to the hanger, wherein the support frame is located in the casing.

19. The endoscope holder according to claim 18, wherein when the hanger is at the first angle position, the support frame is abutted to the slide body.

20. An endoscope holder, comprising:

a holder body;

a hanger pivotably attached to the holder body to move between a first angle position and a second angle position;

a slide member supported on the holder body, the slide member configured to move slidably between a first position and a second position; and a support frame configured to pivot integrally with the hanger, wherein, at the first position, the slide member restricts pivoting of the hanger from the first angle position to the second angle position and, at the second position, the slide member permits pivoting of the hanger from the first angle position to the second angle position, wherein, when the hanger is at the first angle position, the hanger is configured to support an endoscope by hanging the endoscope on the hanger and, when the hanger is at the second angle position, the hanger is configured to not support the endoscope by hanging, wherein the support frame extends in a direction different from the hanger as viewed from a pivot axis of the hanger, wherein the support frame is restricted from pivoting by contacting the slide member when the slide member is at the first position, and wherein the support frame is permitted to pivot without contacting the slide member when the slide member is at the second position.

* * * * *